United States Patent
Nijsen et al.

(10) Patent No.: US 8,691,280 B2
(45) Date of Patent: Apr. 8, 2014

(54) MICROSPHERE COMPRISING AN ORGANIC LANTHANIDE METAL COMPLEX

(75) Inventors: Johannes F. W. Nijsen, Ugchelen (NL); Wouter Bult, Utrecht (NL); Alfred D. van het Schip, Nieuwegein (NL)

(73) Assignees: UMC Utrecht Holding B.V., Utrecht (NL); Stichting voor de Technische Wetenschappen, Utrecht (NL)

( * ) Notice: Subject to any disclaimer, the term of this patent is extended or adjusted under 35 U.S.C. 154(b) by 737 days.

(21) Appl. No.: 12/452,740

(22) PCT Filed: Jul. 18, 2008

(86) PCT No.: PCT/NL2008/050496
§ 371 (c)(1),
(2), (4) Date: Apr. 5, 2010

(87) PCT Pub. No.: WO2009/011589
PCT Pub. Date: Jan. 22, 2009

(65) Prior Publication Data
US 2011/0038793 A1     Feb. 17, 2011

(30) Foreign Application Priority Data
Jul. 19, 2007   (EP) ..................... 07112807

(51) Int. Cl.
*A61K 9/14*   (2006.01)
*A61K 51/12*  (2006.01)

(52) U.S. Cl.
USPC ........ 424/489; 424/1.29; 424/1.37; 424/1.65; 424/9.32

(58) Field of Classification Search
USPC ...................... 424/489, 1.29, 1.37, 1.65, 9.32
See application file for complete search history.

(56) References Cited

U.S. PATENT DOCUMENTS

2006/0057071 A1    3/2006  Wong et al.

FOREIGN PATENT DOCUMENTS

WO    WO 2009/011589 A1    1/2009

OTHER PUBLICATIONS

Oyewumi et al., Drug Development and Industrial Pharmacy, 28(3), 317-328 (2002).*
Hoehn et al., Modern Magnetic Resonance, 1073-1081, (2006).*
Zielhuis et al., Curr. Med. Chem.—Anti-Cancer Agents, 2005, 5, 303-313.*
Zielhuis et al., Lanthanide bearing radioactive particles for cancer therapy and multimodality imaging, 2006, Universiteit Utrecht, Utrecht.
Nijsen et al., Radioactive holmium poly(L-lactic acid) microspheres for treatment of liver malignancies—Polymelkzuur microsferen met radioactief holmium voor de behandeling van lever maligniteiten, Apr. 2001.
Mumper et al., Formation and Stability of Lanthanide Complexes and their Encapsulation into Polymeric Microspheres, Journal of Physical Chemistry, Oct. 15, 1992, pp. 8626-8631, vol. 96, No. 21, American Chemical Society, US.

* cited by examiner

*Primary Examiner* — Michael G Hartley
*Assistant Examiner* — Robert Cabral
(74) *Attorney, Agent, or Firm* — TraskBritt, P.C.

(57) ABSTRACT

The invention provides a microsphere comprising an organic lanthanide metal complex wherein the lanthanide metal is present in an amount of more than 20 wt %, based on total microsphere. The invention further provides a suspension comprising such a microsphere. In addition, the invention relates to a method for preparing said microsphere, and the use of the microsphere(s) or suspension for treating a malignancy and/or obtaining a scanning image.

37 Claims, 7 Drawing Sheets

MICROSPHERE COMPRISING AN ORGANIC LANTHANIDE METAL COMPLEX

The invention relates to the field of radiotherapy and in addition diagnostics.

Radioactive holmium-166 loaded poly (L)-lactic acid (PLLA) microspheres have been proposed as a promising new treatment for liver malignancies in the early 1990's [1]. Since then these microspheres have been studied extensively [2-5]. Holmium-166 ($^{166}$Ho) is a combined beta and gamma emitter. These radioactive microspheres have superior physical and chemical properties than the currently available yttrium-90 microspheres [6]. The holmium loaded microspheres can, for instance, be imaged directly using nuclear imaging, due to the gamma radiation that $^{166}$Ho emits, and MR imaging, due to the high paramagnetic value (X value) of holmium.

The holmium loaded PLLA (poly(L-lactic acid)) microspheres can be prepared by incorporating holmium acetylacetonate into poly(L-lactic acid) by way of solvent evaporation. The stability of the microspheres so obtained is believed to be the result of the interaction of the carbonyl groups of poly(L-lactic acid) with the Ho-ion in the holmium acetylacetonate complex [3]. The poly(L-lactid acid) thus functions as a binder or stabiliser for the formation of the microspheres. There is no indication that microspheres without binder, or with only a small amount of binder, would be stable.

There is, however, a disadvantage to holmium loaded PLLA microspheres, because the loading capacity of these microspheres is limited. The average holmium loading of these microspheres is around 17% (w/w) [3,4].

It is an object of the present invention to provide microspheres that have a substantially higher content of a lanthanide metal and that display at the same time a high stability. A higher lanthanide load, preferably holmium load (w/w), would result in a number of advantages, such as shorter neutron activation time and higher specific activity, which in turn would lead to a reduced amount of microspheres to be administered to patients. In addition, a higher lanthanide load will result in higher and thus improved MRI signals.

Surprisingly, it has now been found that highly stable microspheres with a high lanthanide metal content can be prepared using a lanthanide metal organic compound, whilst no binder or only very small amounts of binder such as poly(L-lactic acid) need to be used.

Accordingly, the present invention relates to a microsphere comprising an organic lanthanide metal complex wherein the lanthanide metal is present in an amount of more than 20 wt %, based on total microsphere.

The reduction of binder material surprisingly does not lead to disintegration of the microspheres. To the contrary, the microspheres in accordance with the present invention are highly stable and contain a high amount of lanthanide, whilst no binder or, if any, only very small amounts of binder are needed.

In the context of the present invention a binder for a microsphere comprising a metal complex is defined as a polymer matrix into which the metal complex can be incorporated, whereby the binder serves to stabilize and form the microsphere.

If any poly(L-lactic acid) is used as the binder it is suitably present in an amount of less than 9 wt %, based on total microsphere. Preferably, the microsphere is free or substantially free of a binder such as, for instance, poly(L-lactic acid). In the context of the present invention, "substantially free" means that the microsphere comprises less than 1 wt % of binder, e.g. poly(L-lactic acid), based on total microsphere.

Suitably, the lanthanide metal to be used in accordance with the present invention is present in an amount of more than 22 wt %, based on total microsphere.

In accordance with the present invention any of the lanthanide metals can be used. Suitably, the lanthanide metal comprises holmium, gadolinium, dysprosium, lutetium, samarium or yttrium Preferably, the lanthanide metal comprises holmium, lutetium, gadolinium or yttrium.

More preferably, the lanthanide metal is holmium or yttrium.

Most preferably, the lanthanide metal is holmium.

Suitably, the lanthanide metal is present in an amount of less than 60 wt %, based on total microsphere.

Preferably, the lanthanide metal is present in an amount in the range of from 25-60 wt %, based on total microsphere.

When the lanthanide metal is yttrium, the lanthanide is preferably present in an amount in the range of from 22-35 wt %, more preferably in the range of from 25-30 wt %, based on total microsphere.

More preferably, when the lanthanide metal is not yttrium it is present in an amount in the range of from 30-60 wt %, based on total microsphere.

Even more preferably, when the lanthanide metal is not yttrium it is present in an amount in the range of from 35-55 wt %, based on total microsphere.

Most preferably, when the lanthanide metal is not yttrium it is present in an amount in the range of from 40-50 wt %, based on total microsphere.

The difference between the amounts to be used in case the lanthanide metal is yttrium or the lanthanide metal is another type of lanthanide metal is due to the difference between the respective atomic mass of yttrium and the respective other lanthanide metals.

Such high amounts of lanthanide metal are very surprising because on the basis of chemical calculations on the starting material to be used one would expect to obtain a microsphere containing much less of the lanthanide metal.

The organic lanthanide metal complex according to the present invention comprises an ion of the corresponding lanthanide and a number of organic molecules with which the ion forms the complex.

Suitably the organic molecules belong to the betadicarbonyl compounds exhibiting the keto-enol tautomerism.

Preferably, the organic molecules are acetylacetonate, 2,4-heptanedione, and 2 (ace toacetoxyethyl)methacrylate.

Most preferably, the organic molecules are acetylacetonate.

The organic molecules in the organic lanthanide metal complex are preferably all the same.

Suitably, the microsphere comprises no other organic compound in addition to the organic molecules.

Preferably, the microsphere in accordance with the present invention is a microsphere.

Preferably, the microsphere in accordance with the present invention has been made radioactive.

The present invention also relates to a powder comprising a number of the microspheres in accordance with the present invention.

The microsphere in accordance with the present invention can very attractively be used in therapeutic applications.

Suitably, the microsphere according to the invention is a radioactive microsphere.

Radioactive microspheres do contain a radioactive element that emits radiation suitable for diagnosis and/or therapy. The radionuclides are (rapidly) decaying (half-life of a few minutes to a few weeks) to, in general, a stable nuclide after emitting ionizing radiation. The most common types of ionizing radiation are (1) alpha particles, (2) beta particles i.e. electrons that are emitted from the atomic nucleus, and (3) gamma-rays (γ) and X-rays. For therapeutic purposes, radionuclides that emit beta (β) or electron radiation, and in some exceptional applications alpha (α) radiation, are applied. The β radiation will damage DNA in the cell which results in cell death.

Often the radionuclide is attached to a carrier material that has a specific function or size which brings the radionuclide to a specific organ or tissue. The design of these carrier compounds is based solely upon physiological function of the target tissue or organ. This carrier material is often an endogenous compound, which is naturally present in the human body. The carrier compounds of the invention are the organic molecules in case that the binder is absent. The organic molecules themselves and the lanthanide metal form the organic lanthanide metal complex and thus the microsphere. If a small amount of binder is added then this compound will help in forming the microsphere. The microspheres of the invention will be adapted in diameter and composition for their specific application.

Nuclear imaging is extremely sensitive to abnormalities in organ structure or function. The radioactive diagnostic compounds can identify abnormalities early in the progression of a disease, long before clinical problems become manifest. Moreover, radiopharmaceuticals comprise the unique ability that they can provide a treatment option by exchanging the diagnostic nuclide for a therapeutic one but using the same carrier. In most of the lanthanides only the radioactivity of the radiopharmaceutical has to be increased as these radionuclides emit often both γ and β-radiation for diagnosis and therapy, respectively. The distribution and biological half-life of the specific therapeutic compound are then mostly very similar to that of the diagnostic compound. For example the use of 166-Ho microspheres for diagnostic application in a screening dose will contain typically 100-500 MBq and for treatment of different types of tumors, e.g. hepatocellular carcinoma (HCC), liver metastases, bone metastases, a dose of up to 16 GBq.

The present invention also provides a therapeutic composition which comprises a radioactive microsphere or a radioactive powder according to the present invention. Such a therapeutic composition can suitably be brought in the form of a suspension before it is administered to an individual. Such therapeutic compositions have the advantage that they require a shorter neutron activation time and that they display a higher specific activity. In addition, a reduced amount of microspheres need to be administered to patients.

Said microsphere of the present invention can be directly generated using a radioactive component, such as radioactive holmium. Preferably however, a non-radioactive microsphere of the invention is firstly generated, followed by irradiation of said microsphere which decreases unnecessary exposure to radiation of personnel. This can avoid the use of high doses of radioactive components and the need for specially equipped (expensive) facilities, such as hot cells and transport facilities.

Said microsphere of the present invention can be used for visualisation of benign lesions in Tuberous Sclerosis by MRI. Said microspheres are used without rendering them more radioactive by means of neutron irradiation.

In one embodiment of the present invention, the therapeutic composition of the present invention comprises a microsphere of the present invention which microsphere is provided with at least one therapeutically active compound, for instance capable of treating a tumour. Such a therapeutic composition is for instance capable of treating a tumour simultaneously by radiotherapy and with a therapeutic action of said therapeutically active compound.

The present invention also provides a non-radioactive therapeutic composition of the present invention, comprising a non-radioactive microsphere of the present invention which is provided with at least one therapeutically active compound, for instance, capable of treating a tumour.

Suitably, the microsphere in accordance with the present invention has a diameter in the range of from 20 nm to 300 μm.

In a particular embodiment of the present invention, the microsphere has a diameter in the range of from 20 nm to 1000 nm, preferably in the range of from 20 nm to 200 nm. Such microspheres can attractively be used for local therapeutic and in addition diagnostic purposes. For local therapeutic purposes the microsphere(s) can suitably be delivered locally via a catheter or via direct injection, whereas for diagnostic purposes the microsphere(s) can be introduced into the body of an individual via parenteral administration, e.g. via injection, infusion, etc.

The microsphere in accordance with the present invention can be prepared using different types of processes. Suitable preparation processes include solvent evaporation processes, solvent extraction processes, spray-drying processes, and inkjet printing processes. Preferably, use is made of a solvent evaporation process.

Hence, the present invention also relates to a method for preparing a microsphere according to the present invention or a powder according to the present invention, comprising the steps of:

(a) dissolving a lanthanide metal organic compound in an organic solvent;
(b) emulsifying this organic phase in an aqueous solution comprising an emulsifier
(c) stirring, and optionally heating, the emulsion obtained in step (b) so as to reduce the volume of the emulsion by evaporating at least part of the organic solvent, thereby obtaining a mixture; and
(d) recovering from the mixture obtained in step (c) the microsphere or the powder.

Suitable emulsifiers include poly vinylalcohol (PVA), poloxamers (Pluronics®), Tween 80, egg phosphatidyl choline, sucrose, etc.

The present invention also provides a suspension comprising a microsphere or a powder in accordance with the present invention.

The suspension according to the present invention suitably comprises a scanning suspension, whereby the microsphere(s) is (are) capable of at least in part disturbing a magnetic field. Said microsphere(s) can be detected by a non-radioactive scanning method such as magnetic resonance imaging (MRI). Preferably said scanning suspension comprises an MRI scanning suspension or a nuclear scanning suspension.

A suspension according to the present invention suitably comprises microsphere(s) of which the composition is capable of essentially maintaining its/their structure during neutron activation.

Magnetic resonance imaging (MRI) provides information of the internal status of an individual. A contrast agent is often used in order to be capable of obtaining a scanning image. For instance ferrite particles and gadolinium-DTPA (diethylaminetriaminepentaacetic acid) complexes are often used in contrast agents for MRI scanning. This way, a good impression can be obtained of internal disorders, like the presence of (a) tumour(s).

After diagnosis, a treatment is often started involving administration of a pharmaceutical composition to a patient.

It is often important to monitor the status of a patient during treatment as well. For instance the course of a treatment and targeting of a drug can be monitored, as well as possible side effects which may imply a need for terminating, or temporarily interrupting, a certain treatment.

Sometimes local treatment in only a specific part of the body is preferred. For instance, tumour growth can sometimes be counteracted by internal radiotherapy comprising administration of radioactive microspheres to an individual. If said radioactive microspheres accumulate inside and/or around the tumour, specific local treatment is possible.

The present invention also relates to the use of a microsphere in accordance with the present invention for the preparation of a scanning suspension. Preferably, the scanning image obtained by using the present microsphere or present powder is a MR scanning image or a nuclear scanning image. In this application the meaning of the word suspension has to be understood as at least including dispersions.

A scanning suspension of the present invention is suitable for determining a flowing behaviour of a microsphere.

A scanning suspension of the present invention is also suitable for detecting a site of angiogenesis. A site of angiogenesis can be detected by determining the flowing behaviour of the microsphere(s) according to the present invention. Typically, the microsphere has a diameter of about 3-5 µm for such an application.

Hence, the present invention also provides the use of the microsphere according to the present invention for detecting a site of angiogenesis.

A scanning suspension of the invention is also very suitable for detecting a malignancy, e.g. a tumour. Preferably, said tumour comprises a liver metastasis.

Therefore, the present invention also provides the use of a microsphere according to the present invention for detecting a malignancy, such as a tumour. Such a tumour can be detected without the need of using radioactive material. Alternatively, microspheres with low radioactivity can be used. After a tumour has been detected, the tumour can be treated with a therapeutic composition according to the present invention comprising the same kind of microspheres as said scanning suspension. In such a therapeutic composition, however, said microspheres are preferably rendered (more) radioactive. Despite the difference in radioactivity, the microspheres of the diagnostic composition for detecting the tumour and the microspheres of said therapeutic composition can be chemically the same.

In one aspect the invention provides a method for detecting a malignancy, e.g. a tumour, comprising
administering to an individual a scanning suspension comprising a microsphere in accordance with the present invention which is capable of at least in part disturbing a magnetic field;
obtaining a scanning image; and
determining whether said image reveals the presence of a tumour.

In another attractive embodiment of the present invention, a microsphere of the present invention has a diameter in the range of from 15-200 µm, more specifically in the range of from 15-100 µm, even more specifically in the range of from 20-100 µm, and most preferably in the range of from 20 to 50 or in the range of from 80-100 µm. A microsphere of such sizes is very suitable for radiotherapeutic purposes. Such a microsphere comprises a diameter sufficiently large to enable said microsphere to be lodged within arterioles. The present invention also relates to the use of a microsphere according to the present invention, wherein the microsphere has a diameter in the range of from 20-100 µm, for embolizing a blood vessel. In using relatively large microspheres, for example in the range of from 50-200 µm, embolisation of tumours, for example bone cancer and tumours due to Tuberous Sclerosis, is possible. When use is made of microspheres having a diameter in the range of from 50-200 µm, embolisation of the vessels leading to said tumour may lead to retardation of tumour growth.

As will be clear from the above, the size of the microsphere in accordance with the present invention may vary considerably, depending on the particular use intended. The skilled person will understand that the desired microsphere size can be obtained by adjusting the relevant process conditions in the solvent evaporation process as described hereinabove.

In yet another embodiment of the present invention, a microsphere of the present invention is administered to a microsphere or complex of interest.

Preferably, such a microsphere or complex of interest comprises a microsphere or complex with a desired function which it can perform within an organism.

More preferably, such a microsphere or complex of interest comprises an organelle or cell of an organism. Most preferably, such a microsphere or complex of interest comprises a liposome or a white blood cell. After administration of a microsphere of the invention to such a microsphere or complex of interest, the microsphere or complex of interest can be detected by a scanning method such as MRI. This way a presence and/or migration of the microsphere or complex of interest can be detected. For instance, a liposome is useful for delivering a nucleic acid of interest to a suitable site for gene therapy. If such liposome has been provided with a microsphere of the present invention it can be determined where said liposome is present inside an organism. It can then be estimated whether a nucleic acid of interest is delivered to a desired site. As another example, after administration of a microsphere of the present invention to a white blood cell, migration of said white blood cell to a site of inflammation, or to a tumour, can be detected using a scanning method such as MRI.

The present invention thus also provides the use of a microsphere of the present invention for detecting a presence and/or migration of a microsphere or complex of interest.

It will be clear from the above that the suspension according to the present invention can be used as such as a therapeutic composition and/or diagnostic composition. In addition, said suspension can be used for the preparation of a diagnostic composition.

Preferably, such a suspension is essentially non-radioactive.

Preferably, the present microsphere is biodegradable, allowing for degradation in an animal body after it has been used, for instance for radiotherapy and/or MRI.

In addition, the present invention provides the use of a microsphere of the present invention for the preparation of a radioactive therapeutic composition. In addition, the present invention provides the use of a microsphere according to the present invention for the preparation of a diagnostic composition.

In terms of the present invention, an individual means an animal, preferably a human.

Preferably, the microsphere in accordance with the present invention is paramagnetic, for instance comprising holmium, gadolinium and/or dysprosium.

The present invention further provides a method for treating an individual suffering from a malignancy, e.g. a tumour, comprising:

administering to said individual a scanning suspension comprising a microsphere which is capable of at least in part disturbing a magnetic field;

obtaining a scanning image of said individual;

determining the distribution of said microsphere within said individual;

administering to said individual a therapeutic composition comprising said microsphere.

Said microsphere in said therapeutic composition is more radioactive than said microsphere in scanning suspension, and/or is provided with at least one therapeutically active compound.

The radioactive therapeutic composition according to the present invention is particularly suitable for treatment of a liver tumour, for instance a liver metastasis.

Of course, other kind of tumours can also be treated by lodging of a blood vessel by a microsphere of the present invention.

The invention furthermore provides a method for preparing a therapeutic composition for treatment of a malignancy, e.g. a tumour, comprising the steps of:

in a first step obtaining a scanning image, more specifically an MRI or nuclear image of a person provided with a scanning suspension of the present invention;

in a second step preparing a therapeutic suspension for treatment of a tumour, using microspheres with essentially the same chemical structure as said microspheres in said scanning suspension, which microspheres are made more radioactive than said microspheres in said scanning suspension.

In one embodiment of the present invention an amount of microspheres is prepared prior to obtaining said scanning image, wherein a first part of said amount of microspheres is used for preparing said scanning suspension and a second part of said amount of microspheres is used for preparing said therapeutic suspension.

The present invention further provides a method for obtaining a scanning image, comprising administering a scanning suspension to an individual and subsequently generating a scanning image of the individual, wherein the scanning suspension comprises a scanning suspension in accordance with the present invention.

The following examples are meant to illustrate the present invention. They do not limit the scope of the invention in any way.

EXAMPLES

Materials

All chemicals are commercially available and were used as obtained. Acetylacetone, 2,4-pentanedione (AcAc; >99.9%), chloroform ($CHCl_3$; HPLC-grade), ethanol ($C_2H_5OH$; absolute, Ph. Eur.), ammoniumhydroxide ($NH_4OH$; 29.3% in water), phosphorus pentoxide (Sicapent®) and Pluronic F68® ($PEO_{100}PPO_{65}PEO_{100}$; MW 9 840-14 600) were supplied by Sigma Aldrich (Steinheim, Germany). Holmium (III) chloride hexahydrate ($HoCl_3.6H_2O$; 99.9%) was purchased from Metall Rare Earth Ltd (Shenzhen, China).

Example 1

Preparation of Holmium Acetylacetonate Complex

The holmium acetylacetonate complex (HoAcAc) was prepared as described previously [2-5]. In short, 10 gram of holmium chloride was dissolved in water and added to an aqueous solution of acetylacetonate (16.6% w/w). The pH of the acetylacetonate solution was adjusted to pH=8.5 with ammoniumhydroxide. Holmium acetylacetonate crystals were formed at room temperature in 24 hours. The crystals were collected and washed three times with water, and dried over Sicapent® under a constant flow of nitrogen for 48 hours.

Preparation of Holmium Acetylacetonate Microspheres

The holmium acetylacetonate microspheres (HoAcAc MS) were prepared using the solvent evaporation technique described previously [2]. 10 grams of holmium acetylacetonate crystals were dissolved in 186 grams of chloroform and added to an aqueous PVA solution (2%). The solution was continuously stirred under a constant nitrogen flow, to evaporate the chloroform. After 40 hours the formed microspheres were collected by centrifugation and washed with water. The washed microspheres were sieved using a wet sieving system that comprised of an Electronic Sieve Vibrator (EMS 755) and an Ultrasonic Processor (UDS 751), purchased from Topaz GmbH, Dresden, Germany. The microspheres were dried at room temperature for 24 hours, followed by drying at 50° C. for 48 hours. After drying the size distribution of the sieved fractions were determined using a Coulter counter (Multisizer 3, Beckman Coulter, Mijdrecht, The Netherlands), with an orifice of 100 μm. The microspheres were suspended in an aqueous solution that contained 1% Pluronic and 10% ethanol (both w/w). Light microscopy was performed to assess the spherical character of the microspheres.

Determination of Holmium Content in HoAcAc MS

The holmium content of the microspheres was determined using the complexometric titration for aluminium that has been described in the European Pharmacopoeia [7]. In short, approximately 50 mg of the dried microspheres is accurately weighed, and dissolved in 1 N NaOH. To this solution 1 N HCl is added and the solution is diluted to 50 ml, 5 grams hexamethylentetramine is added and the pH is adjusted to 5, using 1 N HCl. Approximately 50 mg of xylenol orange is added as an indicator, and the solution is then titrated with 0.01 M EDTA, until the colour changes from purple to yellow. Analyses were performed in triplicate.

The holmium content was measured by inductively coupled plasma optical emission spectrometry (IPC-OES). The microspheres are weighed and destructed at 100° C. with 5 ml 1 N NaOH, which was evaporated to dryness. 15 ml of 2% Nitric acid was added followed by a 1 in 50 dilution. Samples were introduced in an Optima 4300 CV (PerkinElmer; Norwalk, USA) and absorbance was measured at three different wavelengths (345.600, 339.898 and 347.426 nm) to accurately determine the holmium content.

Neutron Irradiation of HoAcAc MS

Stability of the holmium acetylacetonate microspheres was tested after irradiation in a nuclear reactor. The neutron irradiations were performed in the pneumatic rabbit system at the reactor facility in Delft (Department of Radiation, Radionuclides and Reactors, Delft University of Technology, Delft, the Netherlands). The pneumatic rabbit system in the reactor is a means of delivering the microspheres to a position in the reactor, where there is a large abundance of neutrons, and the neutron activation takes place. Approximately 100 mg of the samples was weighed accurately in polyethylene vials (Posthumus Plastics, Beverwijk, The Netherlands), and these samples were irradiated for three hours with a thermal neutron flux of $5\times10^{12}$ $cm^{-2}\cdot s^{-1}$. After one month of radioactive decay the microspheres were examined by light microscopy (LM). Size distribution of the irradiated samples was determined by using the Multisizer-3.

Surface Characteristics of HoAcAc MS

The surface characteristics of the HoAcAc MS (both neutron irradiated and non irradiated) were studied by scanning electron microscopy (SEM), using a Philips XL30 FEGSEM. A voltage of 5 kV was applied. Samples of all different batches were mounted on aluminium stubs and coated with a 10 nm Pt/Pd layer.

Differential Scanning Calorimetry (DSC)

Modulated Differential Scanning Calorimetry measurements were performed in duplicate with a DSC Q1000 (TA Instruments, USA). Approximately five mg sample was transferred on an aluminium pan. The modulation amplitude was set at 1° C. every 60 seconds. Samples were heated with a heating rate of 2° C./min from 20 to 220° C., then cooled to 20° C. at a cooling rate of 2° C./min. After that the samples were heated to 250° C. with a heating rate of 2° C./min. Scans were analysed using Universal Analysis 2000 software (version 3.9A).

would expect on the basis of chemical calculations of the starting material a holmium content of 31.9% (w/w). There was no difference between the two methods to determine the holmium content. Table 1 shows a comparison between the theoretical and measured elemental composition of HoAcAc crystals and measured composition of HoAcAc microspheres (in % w/w). The theoretical amount is calculated as follows.

$$\frac{\text{number of holmium atoms} \times \text{mass of a holmium atom}}{\text{total molecular weight}} \times 100\%$$

TABLE 1

| Element | HoAcAc crystals Ho(AcAc)$_3$·3H$_2$O Structure of HoAcAc crystals | | HoAcAc microspheres Ho$_2$(AcAc)$_3$·4H$_2$O Proposed interactions of AcAc with Ho within the HoAcAc microspheres |
|---------|-------------|----------|----------|
|         | Theoretical | Measured | Measured |
| C       | 34.9        | 36.5     | 27.0     |
| H       | 5.3         | 5.0      | 3.8      |
| O       | 27.9        | 27.1     | 24.2     |
| Ho      | 31.9        | 31.2     | 45.0     |

Raman Spectroscopy

Raman spectroscopy was performed to study the acetylacetonate ligands surrounding the Ho ion in HoAcAc crystals and HoAcAc microspheres. The measurements were carried out on a Kaiser RXN spectrometer equipped with a 70 mW 785 nm diode laser for excitation, a holographic grating for dispersion and a Peltier cooled Andor CCD camera for detection. Spectra were recorded on the samples at room temperature. Detector pixel resolution was about 2 cm$^{-1}$ and 10 scans were accumulated for one spectrum at an exposure time of 3 sec per scan.

Results

Preparation of Holmium Acetylacetonate Microspheres

The yield of the solvent evaporation technique was around 30% of the starting material holmium acetylacetonate, which is in accordance with literature [2,3,5,8,9]. The mean size was around 17 micrometer. The microspheres were spherical and remained spherical after irradiation (FIG. 1a, b).

Determination of Holmium Content

The holmium acetylacetonate microspheres contained 45±0.5% Ho (w/w), which is highly unexpected since one Neutron Irradiation of Holmium Acetylacetonate Microspheres Approximately 100 mg of the samples was weighed accurately in polyethylene vials (Posthumus Plastics, Beverwijk, The Netherlands), and these samples were irradiated for three hours with a thermal neutron flux of 5×10$^{12}$ cm$^{-2}$·s$^{-1}$ resulting in 3.7 GBq of activity (end of bombardment). The inspection of the microspheres after irradiation by LM did not show any irradiation damage of the microspheres. The surface of the microspheres was studied more extensively by SEM.

The size of the microspheres was determined before and after irradiation and data were compared (see FIG. 3a, b). The graph indicates that irradiation does not have an effect on the size distribution of the microspheres.

Differential Scanning Calorimetry (DSC)

The thermograms of the HoAcAc crystals and the HoAcAc MS are distinctly different, the melting temperature Tm has shifted from 130° C. for HoAcAc crystals to 190° C. for HoAcAc MS. The melting enthalpy is in agreement with the data reported in the literature [3].

Raman Spectroscopy

The Raman spectra of the HoAcAc crystals and the HoAcAc microspheres were comparable (FIG. 4). This implies that holmium is surrounded by acetylacetonate in both the HoAcAc crystals and the HoAcAc microspheres. These findings were in agreement with results from infrared measurements (data not shown). The increase of the holmium content, found by elemental analysis, complexometric titration and ICP OES can therefore only be explained by a rearrangement of acetylacetonate around holmium, without changing the structure of acetylacetonate. Taking into account that holmium is surrounded by acetylacetonate ligands, we deduced from the elemental analysis results that per holmium ion probably one and a half acetylacetonate and two water molecules are present in the HoAcAc microspheres.

Discussion

SEM micrographs show that the HoAcAc microspheres were intact after neutron irradiation, and that the surface was smooth (FIG. 3. Neutron irradiation slightly affected the surface of the microspheres (FIG. 3b)). The DSC measurements suggest that upon formation of the microspheres the holmium acetylacetonate complex is rearranged, and that one and a half acetylacetonate molecules leave the complex that is comprised of 1 holmium atom and three acetylacetonate molecules [10]. The thus formed complex is more stable due to more interactions, and will lead to an increase in melting enthalpy. This also explains the difference in holmium content when compared to HoAcAc crystals that has been found by the complexometric titration, elemental analysis and ICP-OES measurements.

As will be clear from the above, in accordance with the present invention microspheres have been produced that consist solely of holmium acetylacetonate, and that are highly resistant to neutron irradiation. It is noted that the loading of these microspheres is no less than 45% Ho w/w, which is as noted before most surprising.

Example 2

Preparation of Gadolinium Acetylacetonate Complex

Gadolinium acetylacetonate (GdAcAc) was prepared using the method as previously described by Nijsen et al. for holmium acetylacetonate [2-3]. Briefly, 166 g of acetylacetone was dissolved in 1 l of distilled water. The pH of the acetylacetone solution was then adjusted to 8.50 by addition of ammonium hydroxide, thereby ionising the acetylacetone to acetylacetonate. 10 g of gadolinium chloride was dissolved in 40 ml of distilled water and added to the acetylacetonate solution, followed by gentle stirring. The solution was then left to stand overnight at room temperature. The crystals were collected by centrifugation (2 000 rpm for 2 min), washed 4 times with distilled water and dried in two steps: first overnight at room temperature, then overnight at 50° C.

Preparation of Gadolinium Acetylacetonate Microspheres

Gadolinium acetylacetonate microspheres were prepared in the same way as described in Example 1 for holmium acetylacetonate microspheres, but 5 g of GdAcAC was solved in 186 g chloroform. Light microscopy was performed to assess the spherical character of the microspheres. FIG. 4 shows a micrograph of the GdAcAc microspheres. The microspheres had a size of approximately 10-20 μm. FIG. 5 shows a SEM micrograph of the GdAcAc microspheres.

The gadolinium content of the GdAcAc microspheres was determined in the same way as described in Example 1. The gadolinium content was 44.4% (w/w).

B. SEM micrograph of HoAcAc microspheres after irradiation.

Figure 1:
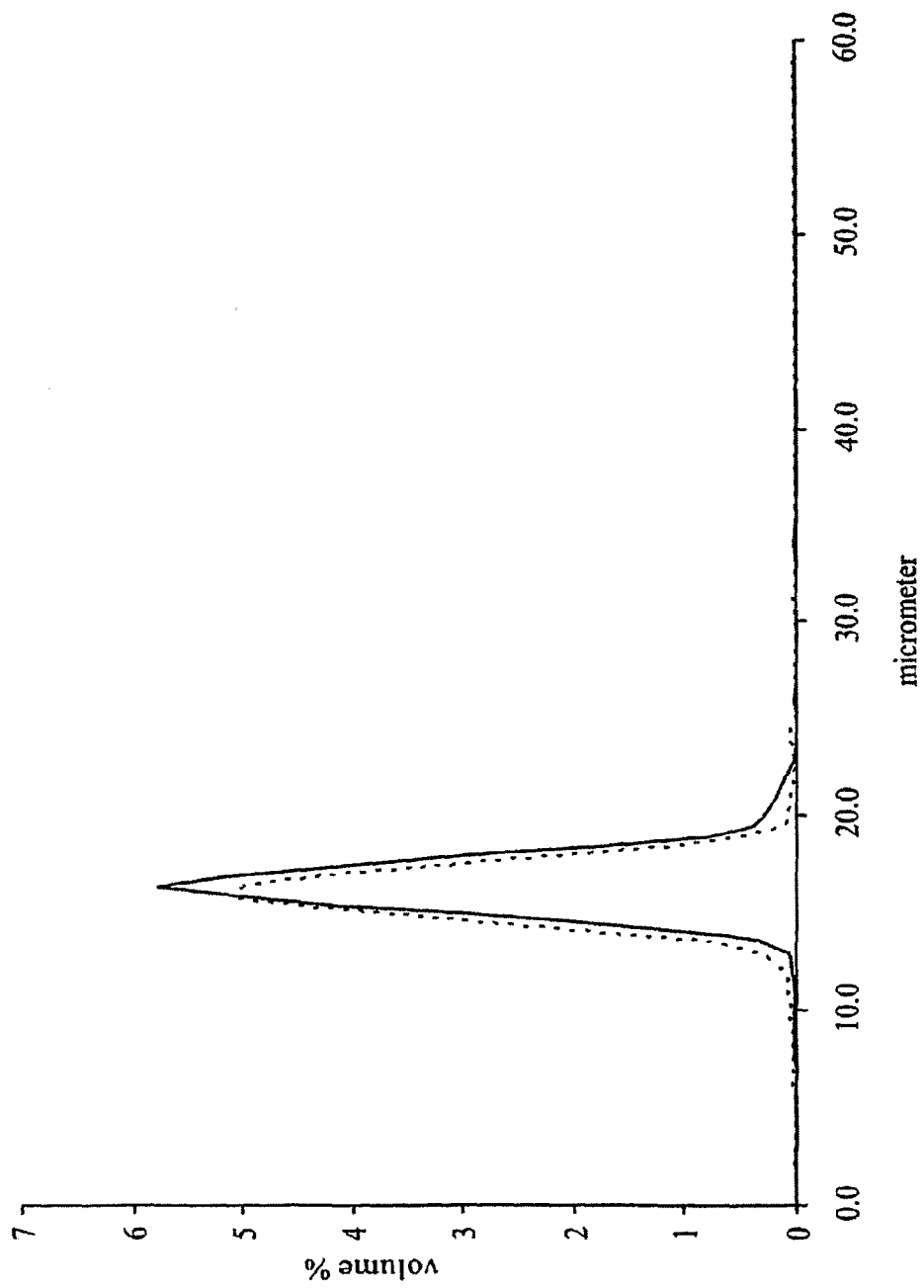
FIG. 1. Size distribution of microspheres of a sieve fraction larger than 15 μm. The solid line represents the particle size before and the dotted line represents the particle size after neutron activation (6 hrs).
Figure 2:
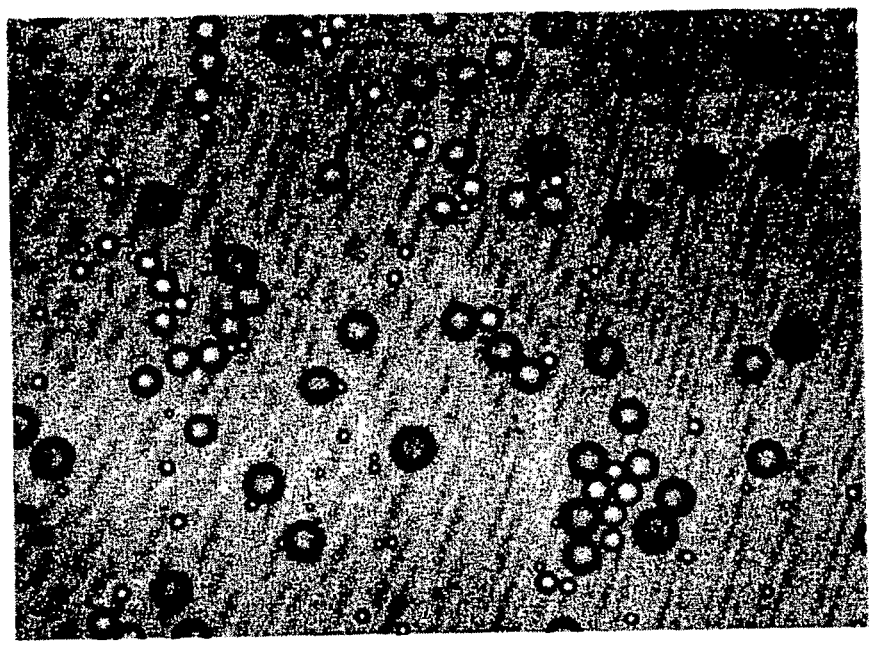
FIG. 2. Light micrograph of freshly produced microspheres, before sieving. This micrograph shows particles between 5 and 25 μm, with a mean size of 15 μm.
Figure 3A:
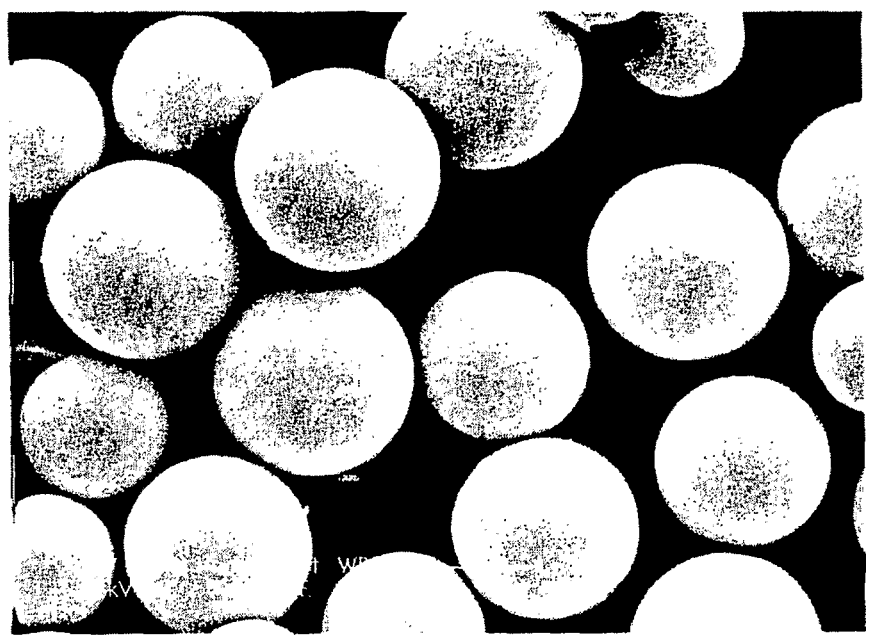
FIG. 3. A. SEM micrograph of HoAcAc microspheres before irradiation.
Figure 3B:
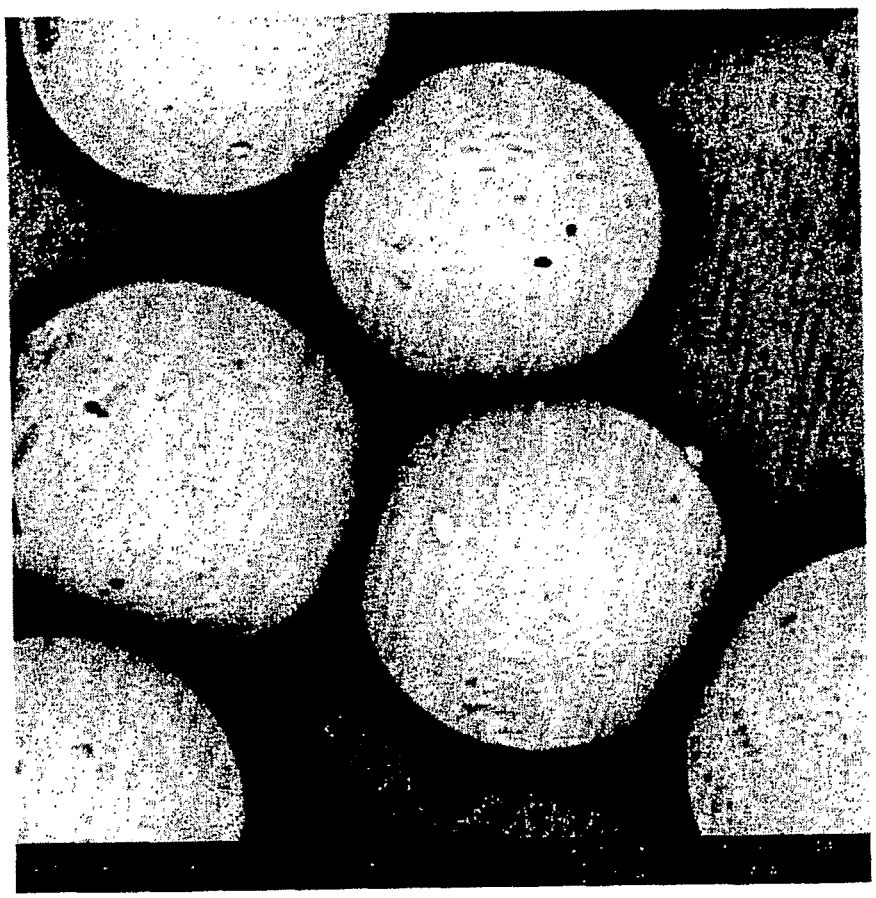
Figure 4:
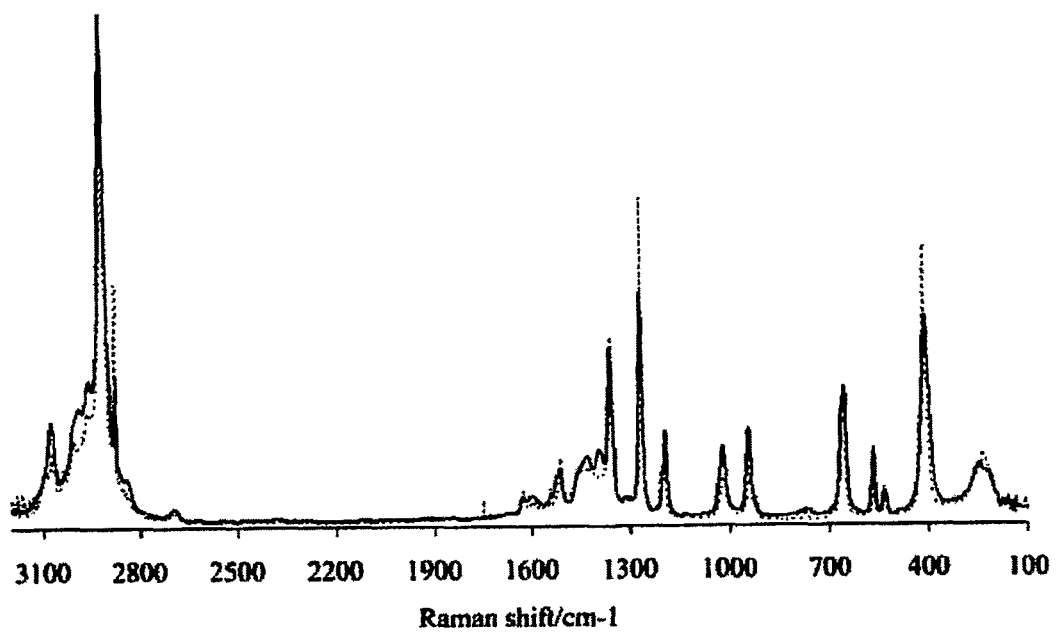

FIG. 4 Raman spectra of HoAcAc microspheres (solid line) and HoAcAc crystals (dotted line), indicating the structural integrity of acetylacetonate in both the crystals and the microspheres.

Figure 5:
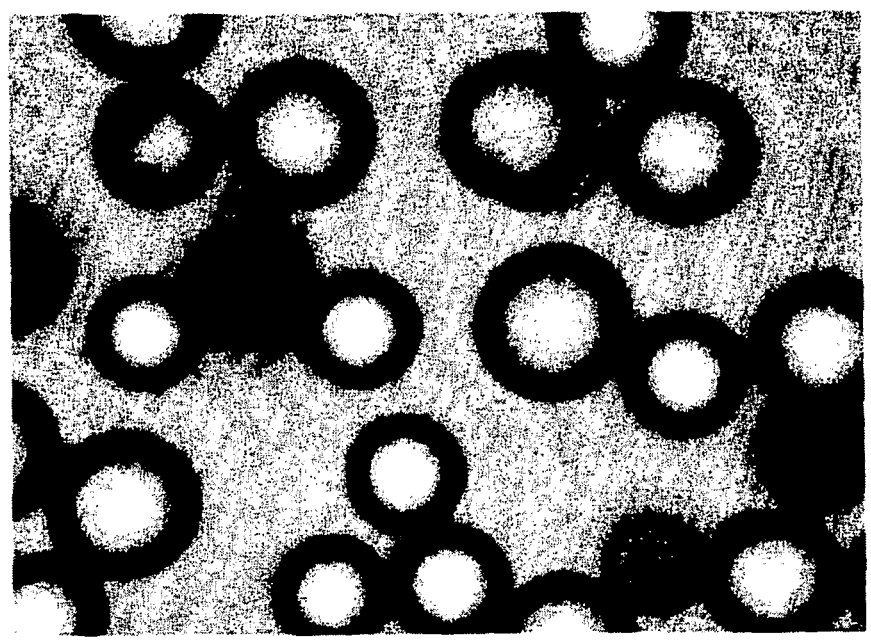

FIG. 5. Light micrograph of GdAcAc microspheres.

Figure 6:
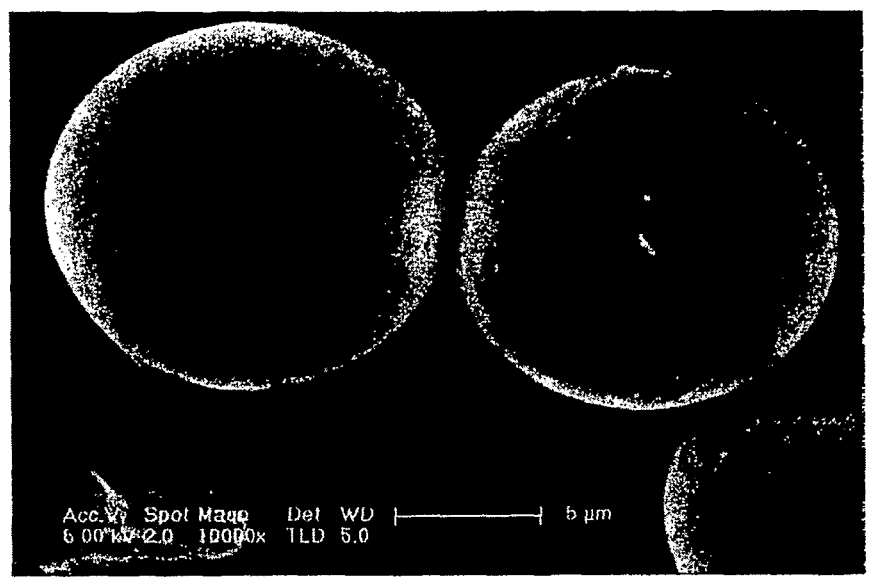

FIG. 6. SEM micrograph of GdAcAc microspheres.

REFERENCES

[1] R. J. Mumper, U. Y. Ryo, and M. Jay, Neutron-activated holmium-166-poly (L-lactic acid) microspheres: a potential agent for the internal radiation therapy of hepatic tumors, J. Nucl. Med., 32 (1991) 2139-2143.

[2] J. F. W. Nijsen, B. A. Zonnenberg, J. R. Woittiez, D. W. Rook, I. A. Swildens-van Woudenberg, P. P. van Rijk, and A. D. van het Schip, Holmium-166 poly lactic acid microspheres applicable for intra-arterial radionuclide therapy of hepatic malignancies: effects of preparation and neutron activation techniques, Eur. J. Nucl. Med., 26 (1999) 699-704.

[3] J. F. W. Nijsen, M. J. van Steenbergen, H. Kooijman, H. Talsma, L. M. Kroon-Batenburg, W. M. van De, P. P. van Rijk, A. De Witte, A. D. van het Schip, and W. E. Hennink, Characterization of poly(L-lactic acid) microspheres loaded with holmium acetylacetonate, Biomaterials, 22 (2001) 3073-3081.

[4] S. W. Zielhuis, J. F. W. Nijsen, R. Figueiredo, B. Feddes, A. M. Vredenberg, A. D. van het Schip, and W. E. Hennink, Surface characteristics of holmium-loaded poly(1-lactic acid) microspheres, Biomaterials, 26 (2005) 925-932.

[5] S. W. Zielhuis, J. F. W. Nijsen, G. C. Krijger, A. D. van het Schip, and W. E. Hennink, Holmium-loaded poly(L-lactic acid) microspheres: In vitro degradation study, Biomacromolecules, 7 (2006) 2217-2223.

[6] R. Murthy, R. Nunez, J. Szklaruk, W. Erwin, D. C. Madoff, S. Gupta, K. Abrar, M. J. Wallace, A. Cohen, D. M. Coldwell, A. S. Kennedy, and M. E. Hicks, Yttrium-90 microsphere therapy for hepatic malignancy: devices, indications, technical considerations, and potential complications, Radiographics, 25 Suppl 1 (2005) S41-S55.

[7] European Pharmacopoeia, 2002.

[8] J. F. W. Nijsen, J. H. Seppenwoolde, T. Havenith, C. Bos, C. J. Bakker, and A. D. van het Schip, Liver Tumors: MR Imaging of Radioactive Holmium Microspheres—Phantom and Rabbit Study, Radiology, (2004).

[9] S. W. Zielhuis, J. F. W. Nijsen, R. R. de, G. C. Krijger, P. P. van Rijk, W. E. Hennink, and A. D. van het Schip, Production of GMP-grade radioactive holmium loaded poly(L-lactic acid) microspheres for clinical application, Int. J. Pharm., 311 (2006) 69-74.

[10] H. Kooijman, F. Nijsen, A. L. Spek, and A. D. van het Schip, Diaquatris(pentane-2,4-dionato-O,O')holmium (III) monohydrate and diaquatris(pentane-2,4-dionato-O, O')holmium(III) 4-hydroxypentan-2-one solvate dihydrate, Acta Crystallogr. C., 56 (2000) 156-158.

The invention claimed is:

1. A microsphere comprising an organic lanthanide metal complex, wherein the lanthanide metal is present in an amount of more than 22 wt % of the microsphere, and wherein the microsphere is free or substantially free of a binder.

2. The microsphere of claim 1, wherein the lanthanide metal is present in an amount of less than 60 wt %.

3. The microsphere of claim 1, wherein the lanthanide metal is present in an amount in the range of 25-60 wt %.

4. The microsphere of claim 3, wherein the lanthanide metal is present in an amount in the range of 30-60 wt %.

5. The microsphere of claim 4, wherein the lanthanide metal is present in an amount in the range of 35-55 wt %.

6. The microsphere of claim 5, wherein the lanthanide metal is present in an amount in the range of 40-50 wt %.

7. The microsphere of claim 1, wherein the lanthanide metal is yttrium.

8. The microsphere of claim 1, wherein the lanthanide metal is selected from the group consisting of holmium, gadolinium, dysprosium, lutetium, and samarium.

9. The microsphere of claim 8, wherein the lanthanide metal is holmium.

10. The microsphere of claim 1, wherein the organic lanthanide metal complex comprises an ion of the lanthanide metal and a number of organic molecules with which the ion forms the organic lanthanide metal complex.

11. The microsphere of claim 10, wherein at least one of the organic molecules is a betadicarbonyl compound exhibiting keto-enol tautomerism.

12. The microsphere of claim 11, wherein the at least one organic molecule(s) is acetylacetonate.

13. The microsphere of claim 10, wherein the organic molecules with which the ion of the lanthanide metal forms the organic lanthanide metal complex are identical.

14. The microsphere of claim 10, wherein the microsphere comprises no other organic compound in addition to the number of organic molecules.

15. The microsphere of claim 1, wherein the microsphere has a diameter in the range of 1-10 µm.

16. The microsphere of claim 1, wherein the microsphere has a diameter in the range of 3-5 µm.

17. The microsphere of claim 1, wherein the microsphere has a diameter in the range of 10-200 µm.

18. The microsphere of claim 1, wherein the microsphere has a diameter in the range of 20-50 µM.

19. The microsphere of claim 1, wherein the microsphere has a diameter in the range of 20-200 nm.

20. The microsphere of claim 1, wherein the microsphere is radioactive.

21. A powder comprising a plurality of microspheres of claim 1.

22. A suspension comprising the microsphere of claim 1.

23. The suspension of claim 22, wherein the suspension is a therapeutic suspension.

24. The suspension of claim 22, wherein the suspension is an MRI scanning suspension or a nuclear scanning suspension.

25. The suspension of claim 22, wherein the microsphere is capable of essentially maintaining its structure during neutron activation.

26. A method for obtaining a scanning image, wherein the improvement comprises:
    utilizing the suspension of claim 22 for obtaining the scanning image.

27. The method according to claim 26, wherein the method comprises determining the microsphere's flowing behavior.

28. A method for detecting a site of angiogenesis, wherein the improvement comprises:
    utilizing the microsphere of claim 1 for detecting the site of angiogenesis.

29. A method for detecting a malignancy, wherein the improvement comprises:
    utilizing the microsphere of claim 1 for detecting the malignancy.

30. A method for treating a malignancy, wherein the improvement comprises:
    utilizing the suspension of claim 22 for the treatment of the malignancy.

31. The method according to claim 29, wherein the malignancy comprises a liver metastasis.

32. A method for detecting a tumor, the method comprising:
    administering to an individual the suspension of claim 22;
    obtaining a scanning image; and
    determining whether the scanning image reveals the presence of a tumor.

33. A therapeutic composition comprising the microsphere of claim 1, wherein the microsphere is radioactive.

34. The method according to claim 30, wherein the malignancy comprises a liver metastasis.

35. The microsphere of claim 11, wherein the organic molecules with which the ion of the lanthanide metal forms the organic lanthanide metal complex are identical.

36. The microsphere of claim 12, wherein the organic molecules with which the ion of the lanthanide metal forms the organic lanthanide metal complex are identical.

37. The microsphere of claim 1, wherein the microsphere consists of ions of the lanthanide metal and betadicarbonyl compounds exhibiting keto-enol tautomerism, with which compounds the ions form the organic lanthanide metal complex.

* * * * *

UNITED STATES PATENT AND TRADEMARK OFFICE
CERTIFICATE OF CORRECTION

PATENT NO. : 8,691,280 B2  Page 1 of 1
APPLICATION NO. : 12/452740
DATED : April 8, 2014
INVENTOR(S) : Nijsen et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 816 days.

Signed and Sealed this
Twenty-ninth Day of September, 2015

Michelle K. Lee
*Director of the United States Patent and Trademark Office*